(12) United States Patent
Daum et al.

(10) Patent No.: US 6,780,338 B2
(45) Date of Patent: Aug. 24, 2004

(54) METHOD FOR PROCESSING A STENT PROCESSED WITH TOOLS CONTAINING MAGNETIZING COMPONENTS

(75) Inventors: Wolfgang Daum, Groton, MA (US); Axel Winkel, Schwerin (DE)

(73) Assignee: MRI Devices Daum GmbH (DE)

( * ) Notice: Subject to any disclaimer, the term of this patent is extended or adjusted under 35 U.S.C. 154(b) by 0 days.

(21) Appl. No.: 10/091,988

(22) Filed: Mar. 5, 2002

(65) Prior Publication Data

US 2003/0078675 A1 Apr. 24, 2003

(30) Foreign Application Priority Data

Mar. 9, 2001 (DE) .......................................... 201 04 145

(51) Int. Cl.[7] ................................................ B44C 1/22
(52) U.S. Cl. ................. 216/22; 148/100; 148/DIG. 51; 29/603.08; 623/901
(58) Field of Search .......................... 623/901; 148/100, 148/200, DIG. 51; 29/603.08, 603.15; 216/22, 75

(56) References Cited

U.S. PATENT DOCUMENTS

| | | | | |
|---|---|---|---|---|
| 6,010,445 A | * | 1/2000 | Armini et al. | 600/3 |
| 6,183,409 B1 | * | 2/2001 | Armini | 600/3 |
| 6,258,182 B1 | * | 7/2001 | Schetky et al. | 148/402 |
| 6,325,824 B2 | * | 12/2001 | Limon | 623/1.2 |
| 6,527,938 B2 | * | 3/2003 | Bales et al. | 205/229 |
| 6,551,341 B2 | * | 4/2003 | Boylan et al. | 606/200 |

* cited by examiner

Primary Examiner—Bruce E Snow
(74) Attorney, Agent, or Firm—Saliwanchik, Lloyd & Saliwanchik

(57) ABSTRACT

The subject invention pertains instruments for use in nuclear spin tomography comprising a metal alloy comprising aluminum, vanadium, and titanium. In a specific embodiment, the subject invention relates to cardiovascular stents which can exhibit a low incidence of artifacts and are viewable in a nuclear spin tomography unit. The subject invention also pertains to a method for processing instruments for use in nuclear spin tomography. Such processing can comprise application of a wet chemical etching solution. In a specific embodiment, the wet chemical etching solution can comprise three parts hydrochloric acid and two parts saltpeter acid.

4 Claims, No Drawings

METHOD FOR PROCESSING A STENT PROCESSED WITH TOOLS CONTAINING MAGNETIZING COMPONENTS

CROSS-REFERENCE TO A RELATED APPLICATION

This application claims priority of German Patent Application No. 20104145.6, filed Mar. 9, 2001.

In today's stent technology it is desirable to use cardiovascular stents that are able to adequately prop open the vessel, that can be accurately positioned and that, and this is new—can be viewed with nuclear spin tomography. Traditional stents are made of stainless steel and show distinct image distortions, so called artifacts. These artifacts occur when materials with high magnetic susceptibility are used.

A goal of the invention is to show means by which the occurrence of artifacts in combination with the stents and nuclear spin tomography can be avoided.

An alloy of 3 percent aluminum by weight and 2.5 percent vanadium by weight, with the remainder being titanium, known as material TIA13V2.5 or material No. 3.7194 or 253.7195 (ASTM Grade 9), shows especially few image artifacts and has sufficient hardness to be suitable for interventional instruments used in nuclear spin tomography.

The above named alloy according to ASTM Grade 9 is harder than an alloy according to ASTM Grade 5 or ISO 3.765 or 3.7165. This would have the following components: 90% titanium, 6% aluminum, and 4% vanadium. The material is more flexible than the so-called ASTM grade 9 material and is therefore more suitable for expanding a stent with the help of a balloon catheter.

Materials that are made to be artifact free but created with tools containing magnetizing components after processing show an increase in screen artifacts which rubbed off the tools. A reduction of surface magnetism can be achieved through dipping in etching solutions which etches the materials the tools are made of. The rub-off from the tools is eliminated by the wet chemical etching solution. Such an etching solution that removes the iron impurities consists for example of 3 parts hydrochloric acid and 2 parts saltpeter acid and can be further reduced with additional parts water in the etching process.

Stents manufactured in the manner here described can be ideally observed in nuclear spin tomography units in magnetic flux density>1.0 Testa. It was possible, for example with an unexpanded stent having a diameter of 1 mm, that was balloon expanded to a diameter of 4 mm, to clearly see all the stent struts, the so-called strats. It was also possible to get a good look inside the expanded stent. So-called in-stent-restenose in the interior of the stent can be seen when a stent has been treated in this manner.

We claim:

1. A method of processing a stent processed with tools containing magnetizing components, comprising:

exposing the surface of a stent processed with tools containing magnetizing components to an etching solution that etches the magnetizing components, wherein exposing the surface of the stein processed with tools containing magnetizing components reduces surface magnetism of the stent, wherein reducing surface magnetism of the stent reduces the occurrence of artifacts from the stent in nuclear spin tomography.

2. The method according to claim 1,
wherein the etching solution etches iron impurities.

3. The method according to claim 2,
wherein the etching solution comprises:
3 parts hydrochloric acid; and
2 parts saltpeter acid.

4. The method according to claim 3,
wherein the etching solution further comprises water.

* * * * *

UNITED STATES PATENT AND TRADEMARK OFFICE
CERTIFICATE OF CORRECTION

PATENT NO. : 6,780,338 B2
DATED : August 24, 2004
INVENTOR(S) : Wolfgang Daum and Axel Winkel It is certified that error appears in the above-identified patent and that said Letters Patent is hereby corrected as shown below:

Column 2,
Line 23, "stein" should read -- stent --.

Signed and Sealed this

Eleventh Day of January, 2005

JON W. DUDAS
*Director of the United States Patent and Trademark Office*